(12) United States Patent
Hnasko et al.

(10) Patent No.: US 12,239,975 B2
(45) Date of Patent: Mar. 4, 2025

(54) BIOSENSOR PLATFORM FOR RAPID DIAGNOSTIC TESTING

(71) Applicant: The United States of America, as represented by the Secretary of Agriculture, Washington, DC (US)

(72) Inventors: Robert M. Hnasko, Pinole, CA (US); Ronald P. Haff, Davis, CA (US); Eric S. Jackson, Lafayette, CA (US)

(73) Assignee: The United States of America, as represented by The Secretary or Agriculture, Washington, DC (US)

( * ) Notice: Subject to any disclaimer, the term of this patent is extended or adjusted under 35 U.S.C. 154(b) by 1080 days.

(21) Appl. No.: 17/154,539

(22) Filed: Jan. 21, 2021

(65) Prior Publication Data

US 2021/0276006 A1  Sep. 9, 2021

Related U.S. Application Data

(63) Continuation-in-part of application No. 16/444,235, filed on Jun. 18, 2019, now Pat. No. 11,415,578.

(51) Int. Cl.
*B01L 3/00*  (2006.01)
*G01N 33/543*  (2006.01)

(52) U.S. Cl.
CPC ...... *B01L 3/5023* (2013.01); *G01N 33/54366* (2013.01); *B01L 2300/0636* (2013.01); *B01L 2300/0825* (2013.01)

(58) Field of Classification Search
None
See application file for complete search history.

(56) References Cited

U.S. PATENT DOCUMENTS

2014/0273269 A1* 9/2014 Liu et al. ............... G01N 33/70
422/69

OTHER PUBLICATIONS

Han et al., "Automated, Universal, and Mass-Producible Paper-Based Lateral Flow Biosensing Platform for High-Performance Point-of-Care Testing," ACS Appl. Mater. Interfaces 2020, 12:1885-1894, published Dec. 9, 2019. (Year: 2019).*
Soh et al., "Strategies for developing sensitive and specific nanoparticle-based lateral flow assays as point-of-care diagnostic device," Nano Today 2020, 30:100831, published online Jan. 3, 2020. (Year: 2020).*

* cited by examiner

*Primary Examiner* — Kaijiang Zhang
(74) *Attorney, Agent, or Firm* — John D. Fado; Richard D. Tuminello

(57) ABSTRACT

The biosensor platform is a rapid point-of-care (POC) device wherein detection of a target substance is performed in a single step using a fully integrated disposable biosensor test system. In one embodiment, the system comprises a horizontally oriented multi-strip test cassette. A user initiates the test by depositing an analyte onto an immunochromatographic test strip sandwiched between a (top) cassette lid and a (bottom) slotted cassette tray. The test strip is held in place by at least one horizontally extending self-adjusting flex plate. The system is structured so that as the analyte flows through the test strip, the analyte reacts with a reagent in the test strip to indicate a presence or absence of the targeted substance as the test strip is held in place by the self-adjusting flex plate.

20 Claims, 17 Drawing Sheets

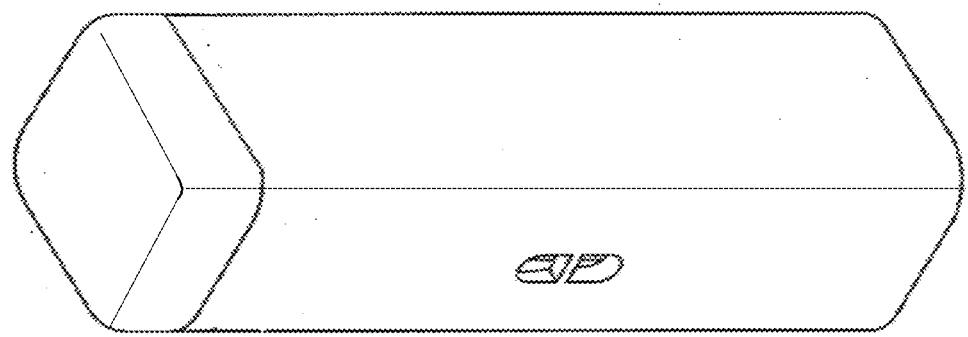
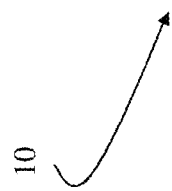
FIG. 1

BIOSENSOR PLATFORM FOR RAPID DIAGNOSTIC TESTING

CROSS-REFERENCE TO RELATED APPLICATIONS

This current disclosure is a continuation-in-part (CIP) of co-pending U.S. patent application Ser. No. 16/444,235, which is hereby incorporated by reference herein in its entirety.

FIELD OF THE INVENTION

The disclosed method and system relates to a single-use biosensor platform designed to perform a rapid immunoassay. The system uses modular components that enable users to perform simple point-of-care (POC) tests in a portable setting. Specifically, the method and system described herein relates to a modular biosensor platform that fully integrates all the necessary assay components in a small single-use disposable platform for the rapid detection of analytes from either solid or liquid substrates using an immunoassay test strip format.

BACKGROUND OF THE INVENTION

There is an expanding demand for rapid POC testing in the general health and food safety areas. These types of tests can provide inexpensive and easy-to-use detection options for allergens, pathogens, toxins, adulterants and other environmental contaminants from the farm to the fork. Based on current data, the market for these types of tests is projected to expand at a rate of about 10% annually—and eventually grow to more than $38 billion by 2022. North America accounts for the greatest share of the market at a projected market size of $16B, with the largest growth occurring in lateral flow assays, detection of infectious diseases, and 'at home' and personal end-user health management segments.

The most successful lateral flow devices (to date) include detection of human chorionic gonadotropin (hCG), a hormone associated with human pregnancy, and assays that detect the presence of specific (usually illicit) drugs in the system of a test subject. These assays utilize direct liquid urine samples and consequently device designs do not require a liquid sample extraction buffer and precision liquid delivery mechanism.

Many applicable tests, particularly in agriculture, require extraction of solid into a liquid or the pH buffering of a liquid sample coupled to a mechanism to deliver a limited volume with precision to a test strip for testing to proceed. To achieve this, current state of the art lateral flow devices provide separate poorly integrated components relying on multi-step procedures to perform simple tests.

These assay kits often include: 1) an immunochromatographic test strip in a two-piece plastic housing stored dry in a desiccant bag; 2) a separate container with liquid sample extraction buffer; and, 3) a disposable liquid transfer pipette. The tests proceed after the end-user transfers a volume of liquid from the sample extract to a sample port on the test strip housing in a horizontal orientation. End-user error in liquid delivery volume and/or location is a significant problem. Moreover, multi-step science-kit methodologies are frequently impractical, prone to error, cumbersome to perform and therefore less desirable to end-users in field locations.

To address these issues, the inventors have developed modular biosensor platforms that integrate an immunoassay test strip with sample extraction and liquid delivery in a small, easy-to-use and disposable format. This biosensor platforms provides users with rapid and accurate test results in a single-step with minimal end-user training. The inventors' flexible biosensor platforms is comprise small field portable units that provides a stand-alone test that includes fully integrated sample extraction capability and liquid delivery to immunochromatographic test strips.

These biosensor systems are suitable for the rapid detection of target analytes from a wide range of liquid and solid substrates and are compatible with most standard lateral flow test strip dimensions. Components of the modular biosensor platform are designed for ease of manufacturing and assembly allowing interchangeable components to accommodate different test and liquid extraction buffer combinations. The inventors' modular biosensor platforms are designed to be compatible with a separate digital reader tool that allows rapid digital porting of test strip results onto a data platform for recording and analyzing the resulting test data.

SUMMARY OF THE INVENTION

This disclosure is directed to a modular biosensor system that is used to test for the presence or absence of a target analyte in a substrate. The system includes a test receptacle comprising an outer sleeve, and a test capsule containing a liquid. The sleeve includes a central opening structured to hold a liquid filled capsule, and a test strip chamber configured to hold a standard immunochromatographic test strip. The base of the sleeve includes a restrictor port which allows liquid to flow from the sleeve central opening to the test strip chamber. The sleeve also includes a resilient flex plate that extends into the test strip chamber and abuts the test strip.

In operation, a user adds a sample to the liquid filled capsule and initiates a test by rupturing the capsule. The analyte liquid flows out of the capsule, through the restrictor port and into a bottom portion of the sleeve. The restrictor port—in combination with the test strip chamber and a bottom portion of the test strip, forms a structural relationship that functions to create a capillary force that wicks the analyte from the bottom of the sleeve, through the restrictor port and up the test strip. As the analyte moves up the test strip, the flex plate holds the test strip in position and maintains material contact allowing the analyte to move upwardly through the test strip and migrate through test strip materials. The user reads the test results through a test window opening which allows the user to see the results shown on a top portion of the test strip.

BRIEF DESCRIPTION OF THE DRAWINGS

FIG. 1 is an elevational perspective view of a preferred embodiment of the assembled biosensor system.

FIG. 12 shows the multi-test strip cassette embodiment prior to loading the biosensor/multi-test strip cassette with an immunochromatographic test strip.

DETAILED DESCRIPTION OF PREFERRED EMBODIMENTS

Figure 2:
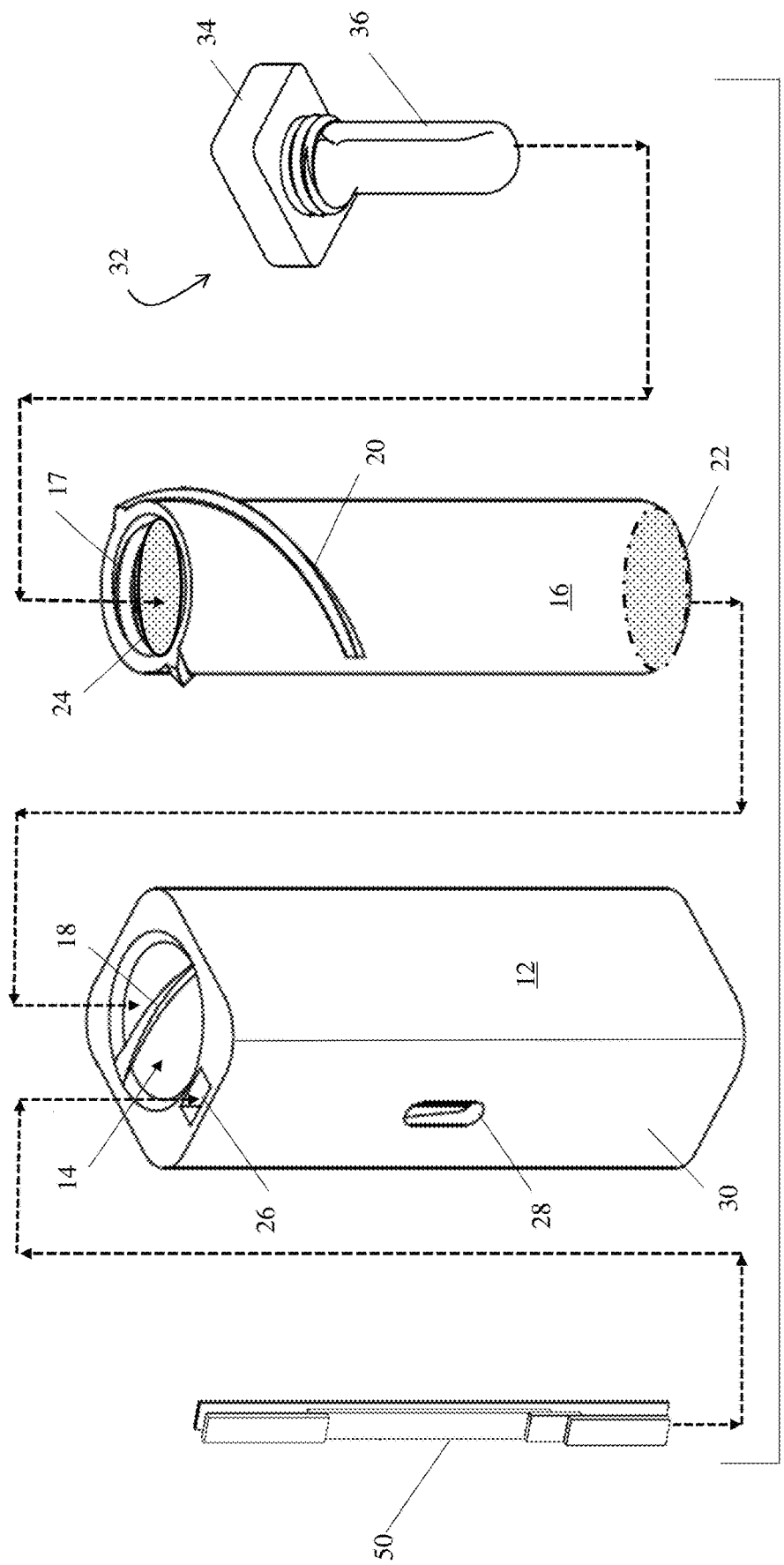
FIG. 2 is an exploded/assembly view of the biosensor system.

As generally shown in FIGS. 1-17, the system described herein comprises various embodiments of an integrated modular biosensor. FIG. 1 shows one embodiment of the modular biosensor system 10 in the fully assembled configuration. FIG. 2 shows an assembly/exploded view of the modular biosensor system 10 shown in FIG. 1. As shown in FIG. 2, the system 10 comprises a capsule sleeve 12 with a central interior opening 14 of sufficient size to accommodate a cylindrical water-tight liquid capsule 16. The capsule 16 includes an open top end 24 and a frangible bottom 22. The top end 24 may be open, or the top end 24 may also be covered by a modular frangible adaptor or cap 32. The capsule 16 may be empty or the capsule 16 may be pre-filled with a buffering liquid, or the liquid may comprise any fluid known in the art consistent with needs of a user, and the physical limitations of the capsule 16.

In one preferred embodiment, as best shown in FIGS. 1 and 2, the sleeve 12 is generally cubic with a vertical height of 63 mm, a horizontal width of 20 mm, and a horizontal length of 22 mm. The capsule 16 has a cylindrical shape with a height in the range of 55 mm, and a diameter in the range of 7 mm. However, in alternative embodiments, the dimensions of the components 12 and 16 may be modified to meet the needs of an individual user.

In the preferred embodiment, the sleeve 12 central opening 14 includes an interior screw thread 18 that corresponds to an exterior screw thread 20 on the analyte liquid capsule 16. A user must screw the capsule 16 down into the central opening 14 of the sleeve 12 to initiate a test. The necessity to screw the capsule 16 down into the sleeve 12 prevents the test process from being inadvertently initiated until the user is ready to begin the test. Essentially, the test will not begin until a user has taken a positive intentional action by screwing the capsule 16 into the sleeve 12 central opening 14. When the test is initiated, the sleeve 12 holds the capsule 16 in a generally vertical position for the duration of the test.

As further shown in FIG. 2, the capsule 16 includes threads 17 configured to receive a cap 32. The cap 32 comprises an upper portion 34 that is visible above the sleeve 12, and a lower portion 36 that may comprise a scoop or other tool-type mechanism. In alternative embodiments, the lower portion 36 of the cap 32 may comprise a variety of tools including a spoon, spatula, grinder, paddle, fork, knife, plug, a punch, a measuring device, a filter, or any other sampling/utility tool that can be contained within the capsule 16. The tool comprising the lower portion 36 of the cap 32 may function to cut or otherwise remove or gather material to be added to the capsule 16. In the preferred embodiment, the cap 32 is a standard size, and the configuration of the cap 32 is based on the needs of a user.

In addition to a cap 32, the threads 17 may be configured to receive a flow adaptor or tubing connection so that fluid can be easily made to flow through the cap 32 and into the capsule 16. The threads 17 may comprise a snap lip-type connector or any other connecting means required to connect the capsule 16 with a desired attaching top/mechanism. Alternatively, the upper portion 34 of the cap 32 may be comprised of a resilient material so that a needle can penetrate the cap 32 and inject a fluid directly down into the capsule 16.

The capsule sleeve 12 also includes a narrow, elongated test strip sleeve/chamber 26 designed to accommodate a standard paper test strip 50 that is (preferably) 4-5 mm in width and about 60 mm in length. The test strip chamber 26 is positioned in a front wall 30 of the sleeve 12 and extends the majority (62 mm) of length of the sleeve 12. In operation, a user slides the test strip into the test strip chamber opening 25 and continues to slide the test down into the test strip chamber 26 until the bottom of the test strip 50 abuts a test strip stopper 42. The test strip stopper 42 comprises a pair of pins that support the bottom corners of the test strip 50. The test strip stopper pins may extend horizontally outward from a wall of the test strip chamber 26. In alternative embodiments, the test strip stopper pins 42 may extend upwardly from the bottom 41 test strip chamber 26.

The test strip 50 is preferably comprised of industry standard materials such as plastic-backed nitrocellulose and specialized layered paper/media containing analyte detection reagents and other chemical indicators, as required for a specific test. In the preferred embodiment, the test strip comprises at least a sample pad, 46, a conjugate release pad 47, and a nitrocellulose membrane 48 (see FIGS. 7 and 13). In alternative embodiments, the test strip 50 may be comprised of any material known in the art. In one (simple) embodiment, the test strip 50 utilizes antibodies that specifically recognize and bind a target substance conjugated to a molecular reporter such as gold nanoparticles. Single substance detection can include a target-specific antibody striped on a nitrocellulose substrate at a test line (T) and an appropriate target analyte independent antibody striped at a control line (C).

Figure 6:
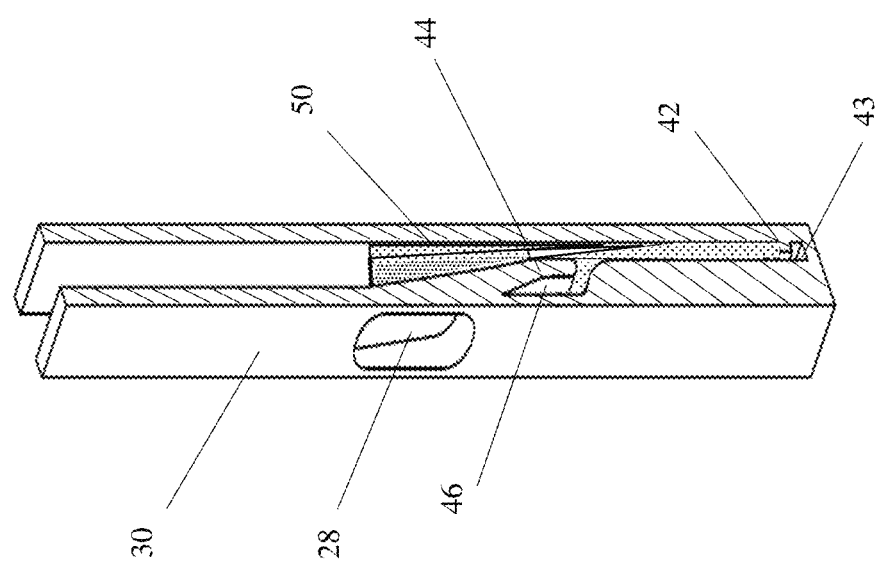
FIG. 6 is a perspective sectional of the front portion of the sleeve.

The capsule sleeve 12 also includes a test result window 28 on the capsule sleeve's front panel 30, as best shown in FIG. 6. The test window 28 comprises an aperture in the front panel 30 of the sleeve 12. The test window 28 is positioned so that a user can see a designated portion of the test strip 50 positioned in the test strip chamber 26. An observer can directly read the results of the test from the test strip 50 through the test window 28. Alternatively, the test window 28 may be configured so that a digital test result reader can read the test results digitally.

FIGS. 3-7 show the interior components of the outer sleeve 12. The bottom 41 of the central opening of the sleeve 12 includes an angular spike 38 that functions to puncture or break the bottom of capsule 16 when the user twists the capsule 16 into place, and thereby liberates the liquid in the capsule 16. In alternative embodiments, the "spike" 38 may comprise any configuration consistent with the function of piercing the test liquid analyte capsule 16. In further alternative embodiments, the capsule 16 may simply slide into the sleeve 12 without the use of a threaded connection 18, 20, or there may be a snap lip-type receiver in the bottom 41 of the central opening of the sleeve 12, or another means of mating and locking the capsule 16 into the bottom 41 of the sleeve 12.

Figure 3:
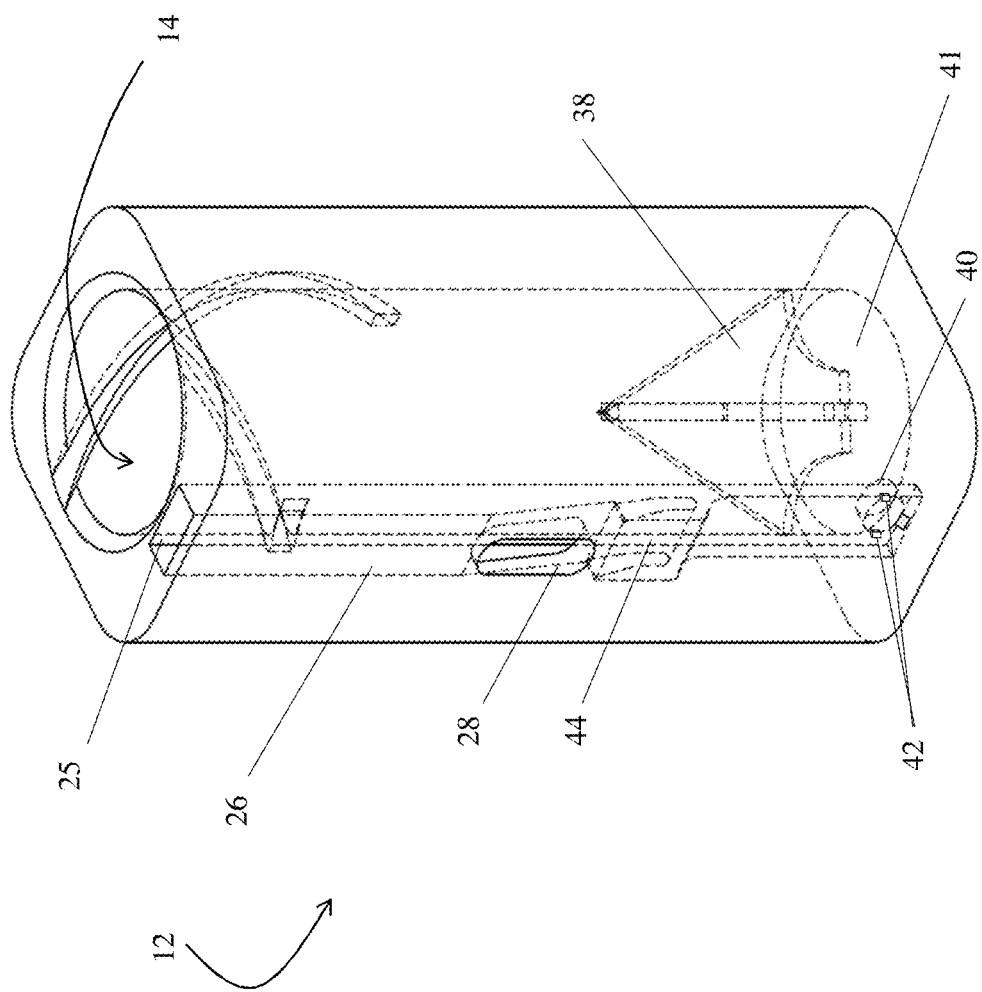
FIG. 3 is an elevational hidden line drawing showing the internal components of the capsule outer sleeve.
Figure 4:
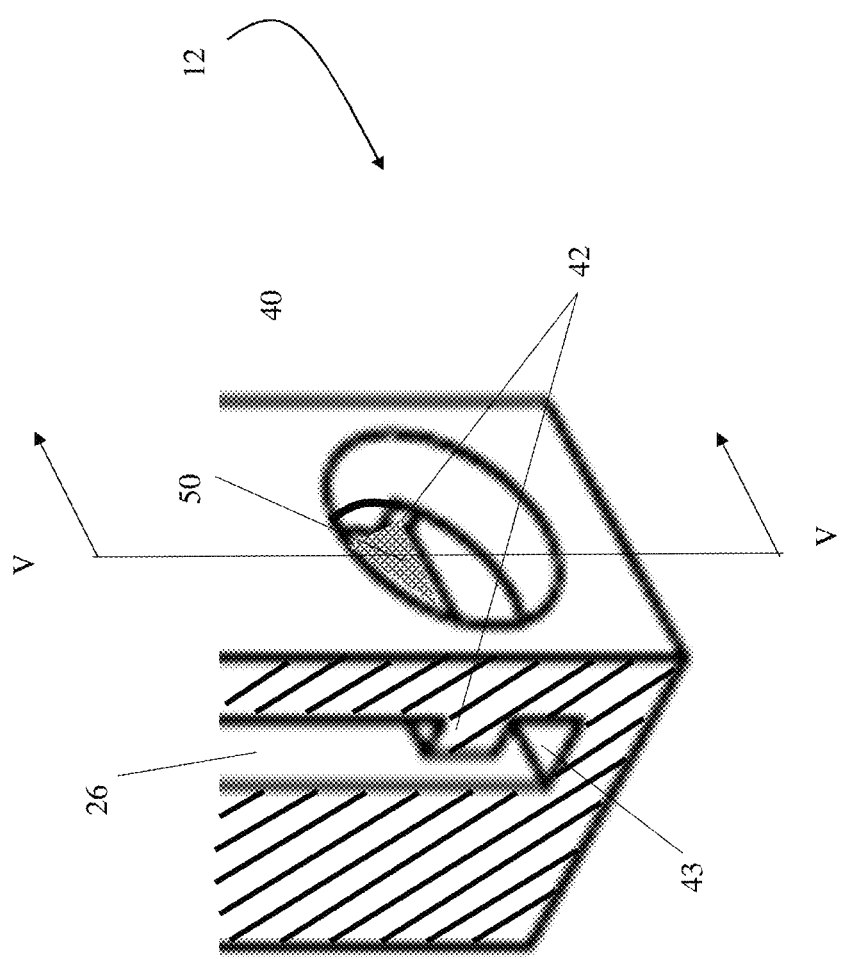
FIG. 4 is a perspective sectional view of the bottom portion of the sleeve, including the section line V-V.
Figure 5:
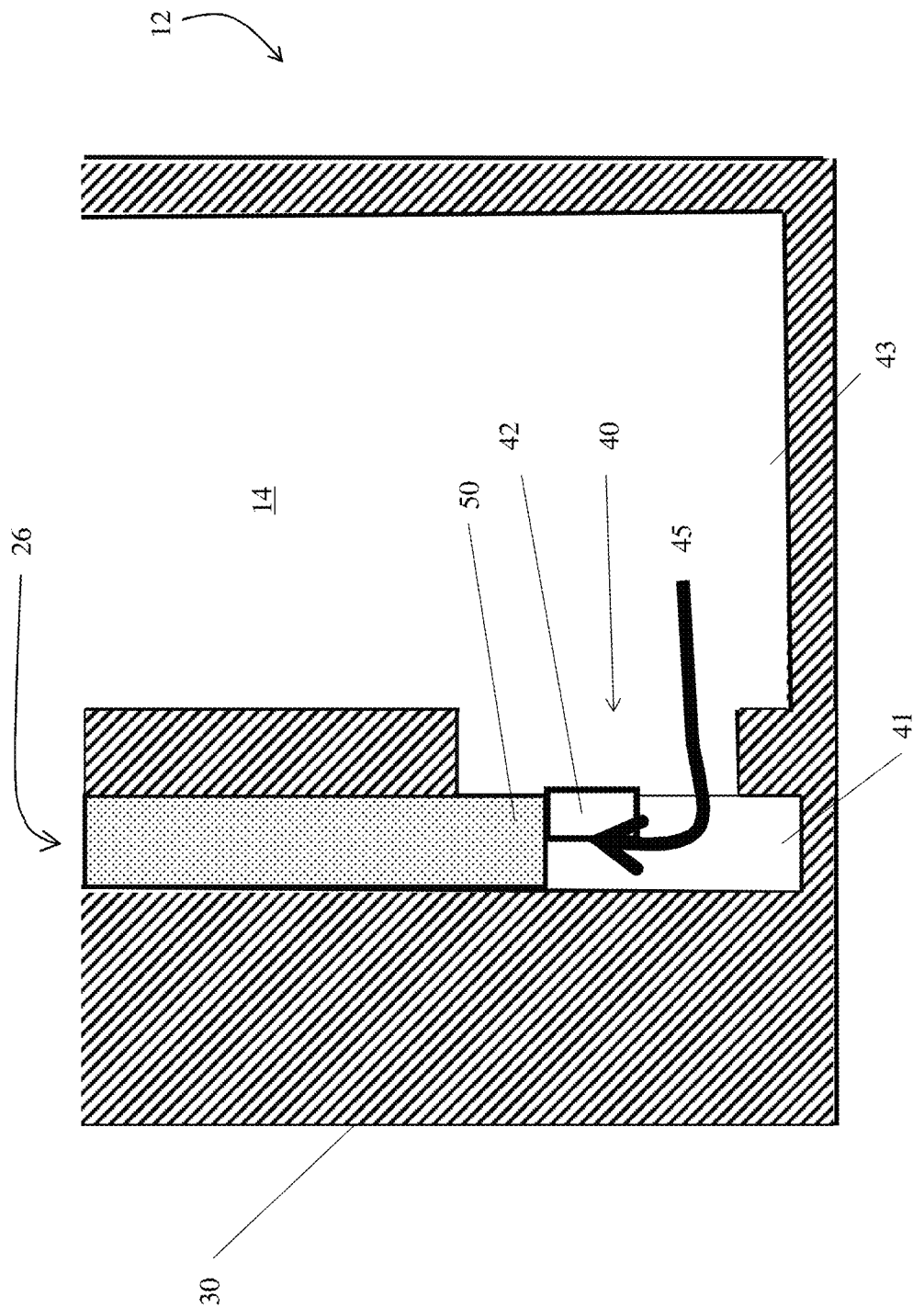
FIG. 5 is a sectional view of the bottom portion of the sleeve along the section line V-V shown in FIG. 4.

FIGS. 3, 4, and 5 show a restrictor port 40 positioned near the bottom 43 of the test strip chamber 26. The restrictor port 40 connects the test strip chamber 26 to the central interior opening 14 of the sleeve 12. More specifically, as best shown in FIGS. 4 and 5, the restrictor port 40 connects the bottom 43 of the test strip chamber 26 to the bottom 41 of the central opening 14 of the sleeve 12. In the preferred embodiment, the restrictor port 40 has a diameter of 3 mm. The size and placement of the restrictor port 40 are crucial to the ability of a user to conduct an accurate test. The restrictor port 40 is designed to modulate and control movement of the analyte fluid from the capsule 16 to the test strip 50.

Specifically, as best shown in FIG. 5, the restrictor port 40—in combination with the test strip chamber 26 and the bottom portion of the test strip 50—forms a structure that functions to create a capillary force wicking (as indicated by the arrow 45) fluid from the central interior opening 14 through the restrictor port 40 and upwardly to the test strip 50. The test strip 50 then "wicks" (via capillary action) the fluid up to the test window 28—which corresponds with the portion of the test strip 50 indicating the results of the test. In the preferred embodiment, the test fluid is water-based or has fluidic properties that are similar to water. In alternative embodiments, the fluid may comprise alcohol, acids, bases, or any other substance consistent with the capability of capillary action-type movement.

The bottom end of the test strip 50 rests on the test strip stopper 42, which maintains the position of the test strip 50 above the bottom 43 of the test strip chamber 26. As shown in FIG. 3, the test strip stopper 42 extends horizontally from an inner wall of the test strip chamber 26. As best shown in FIG. 4, the test strip 50 abuts and partially covers/obstructs the restrictor port 40 so that the fluid contacts the test strip 50 as the fluid flows through the restrictor port 40. The placement of the test strip 50 partially across the restrictor port 40 but above the bottom 43 of the test strip chamber 26 means that the test strip 50 is exposed to the liquid passing through the restrictor port 40, but the test strip 50 does not necessarily sit in the residue that gathers at the bottom 43 test strip chamber 26.

Figure 7:
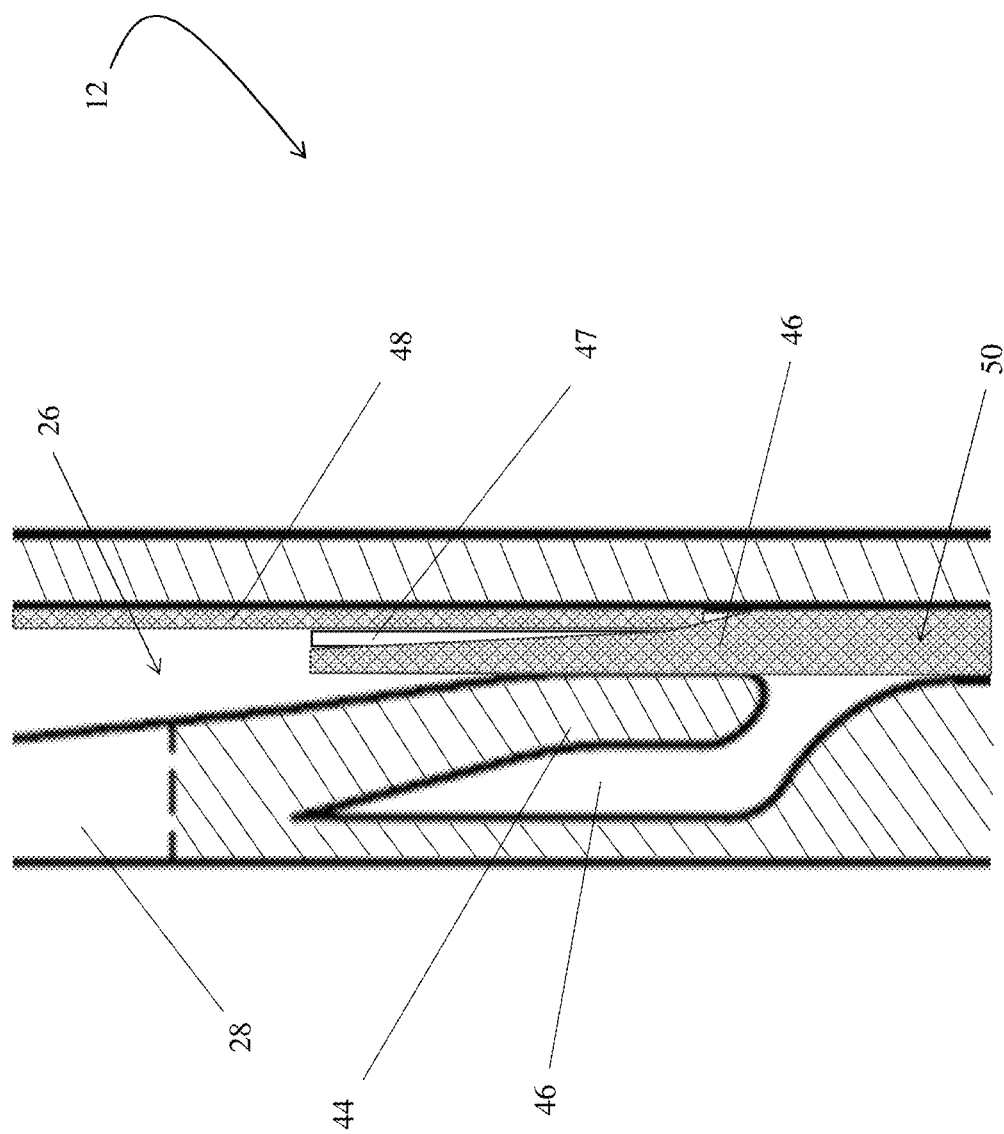
FIG. 7 is an enlarged cross section showing the flex plate contacting the test strip.

As shown in FIGS. 3, 6, and 7, a flex plate 44 is positioned above the restrictor port 40 and below the test window 28 on a front portion 30 of the sleeve 12. The flex plate 44 is comprised of a self-adjusting resilient material. For the purposes of this disclosure, the term "resilient" means rigid but capable of bending/flexing significantly without breaking. In the preferred embodiment, the flex plate 44 is angled downwardly from a vertical interior wall of the test strip chamber 26 and has a generally peninsular/elongated cross section. In the preferred embodiment, the flex strip 44 extends downwardly into the test strip chamber 26 at an angle of about 14 degrees. The flex plate has a horizontal width of about 4.6 mm, and a downwardly-angled length of about 7 mm. In alternative embodiments, the flex plate 44 may have a generally ">" shape where the nose of the ">" contacts the test strip.

As best shown in FIGS. 6 and 7, the flex plate 44 holds the test strip 50 in place—but does not exert enough force on the test strip 50 to damage the test strip 50 materials or impair the test strip's 50 function. The flex plate 44 is sufficiently flexible to allow for different material tolerance thicknesses used in test strip 50 construction—which facilitates the transfer of chemical reagents between the separate material components of a test strip 50. The flex plate 44 is also designed to limit excess liquid flow vertically up the test strip 50 or outside of the test strip, which may skew the test results. The area 46 behind the flex plate 44 comprises an overflow zone where the excess fluid may collect without impairing the test process.

As best shown in FIG. 7, in the preferred embodiment, the flex plate 44 abuts and exerts pressure on a transitional area of the test strip 50. Specifically, on a standard test strip 50, the flex plate 44 exerts pressure on the area of the test strip where the sample pad 46, the conjugate release pad 47, and the nitrocellulose membrane 48 overlap and interface. The self-adjusting pressure of the flex plate 44 ensures solid contact and fluidic communication between the three layers 46, 47, 48 so that test liquid is successfully transferred. The pressure plate 44 ensures (to the extent practical) capillary flow dictated by the porous desiccated materials that comprise test strip layers 46, 47, 48. Test liquid will continue to flow through the nitrocellulose membrane 28 to another material (not shown) at the top of the test strip 50 that serves as an absorbent sink which, when saturated, ends the capillary draw and prevents backflow action.

In operation, in the preferred embodiment, a user breaks the frangible seal 24 (if there is one) or unscrews the sealing cap on the top capsule 16 and adds a sample material (which may be solid or liquid) to the capsule 16. The user may use the (for example) scoop 36 on the bottom of the cap 32 to break the seal and/or prepare the sample material. Depending on the nature of the test, the capsule 16 may or may not hold a buffer fluid or other media required for the test. For example, in the case of a simple urine test, a urine sample is added directly to an empty capsule 16. When the sample preparation is complete, the cap 32 is screwed (or otherwise connected) to the capsule 16.

To initiate the test, a user screws the capsule 16 down into the sleeve 12 so that a spike 38 pierces the bottom 22 of the capsule 16 and an analyte liquid (or a solid-liquid mix) flows out of the capsule, through the restrictor port 40, and into the bottom 41 of the sleeve 12. As liquid continues to flow from the capsule 16, the liquid flows through the restrictor port 40 and into the bottom 43 of the test strip chamber 26. The restrictor port 40, in combination with the test strip chamber 26 and the bottom portion of the test strip 50—forms a structure that functions to create a capillary force that "wicks" fluid from the capsule 16 in the central interior opening 14 through the restrictor port 40 and upwardly to the test strip 50.

The liquid in the test strip 50 is drawn upwardly (by capillary action) until the liquid reaches a position adjacent to the flex plate 44. The flex plate 44 exerts sufficient pressure on the test strip 50 to maintain the position and stability of the test strip 50 and facilitate the transfer of analyte liquid between test strip materials. The liquid continues to flow upwardly until the liquid reaches a position corresponding to an absorbent pad at the top of the test strip. Test results are resolved on the test strip 50 and are interrogated at the test window 28, where the presence or absence of a target analyte is generally indicated by a visual indicator system, thereby completing the test. A user then reads the results of the test (as indicated on the test strip) either directly with his eyes, or electronically with a digital scanner/camera/reader.

Figure 8:
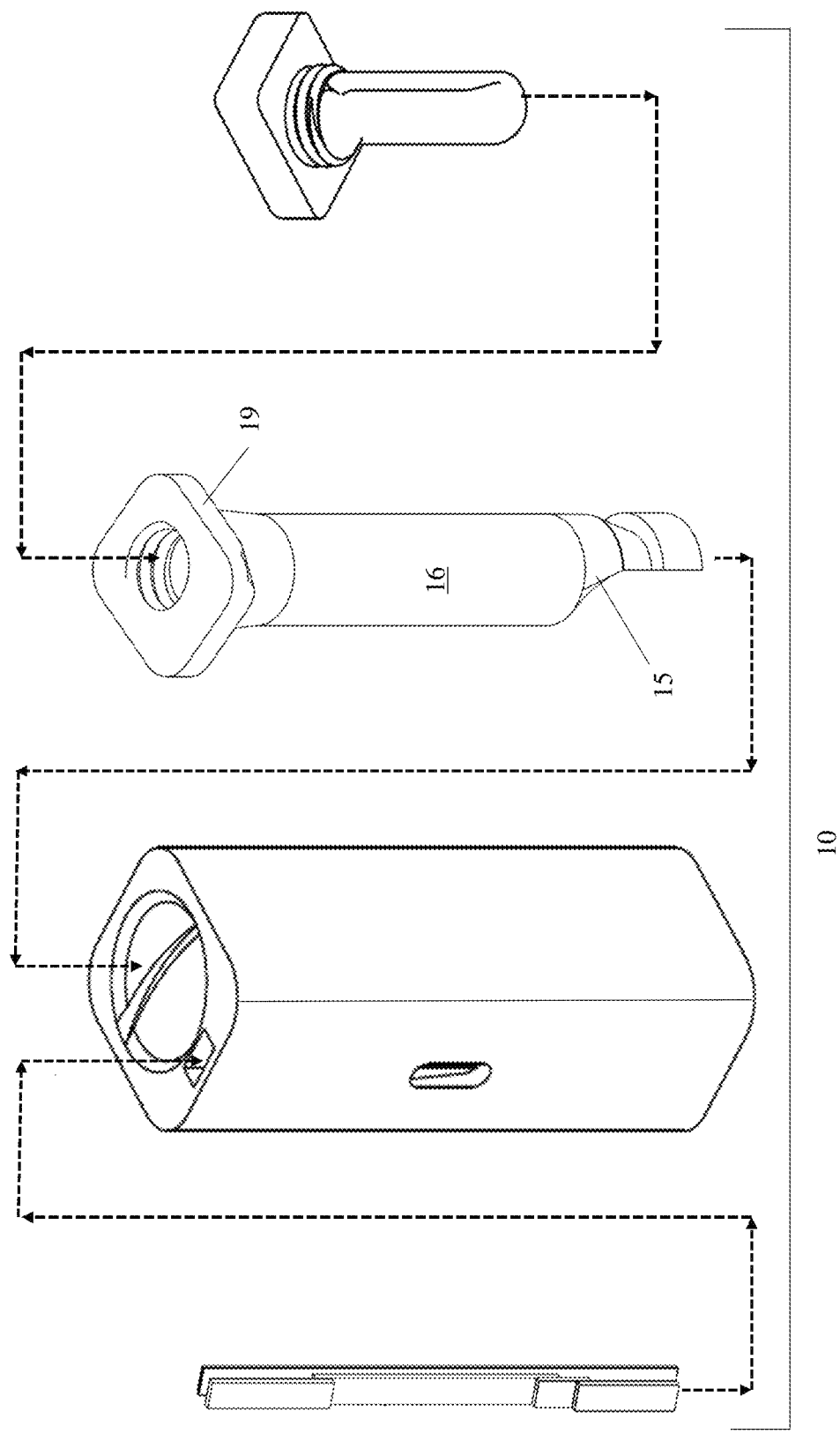
FIGS. 8 and 9 show an alternative embodiment.
Figure 9:
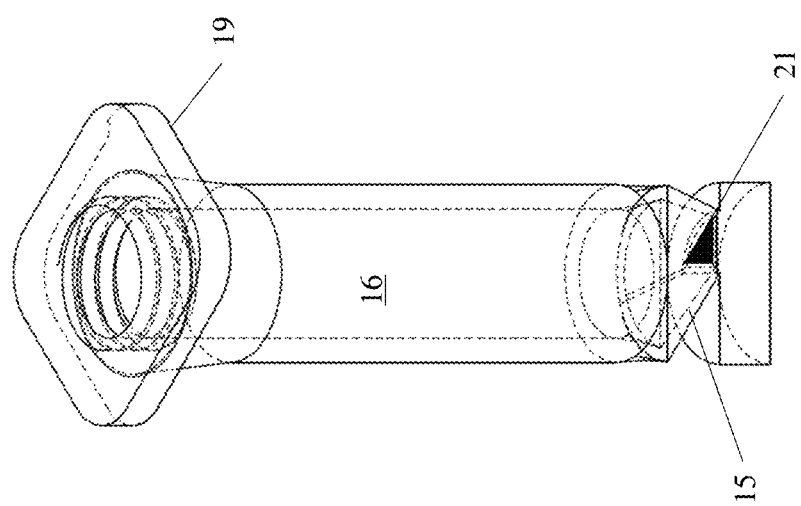

FIGS. 8 and 9 show an alternative embodiment of the system 10. This embodiment involves breaking the bottom of the capsule rather than puncturing to allow fluid to flow. This allows the capsule to be seated and integrated within the housing with no parts in the base of the sleeve 12 sticking out and interfering with the flow of the fluid from the capsule 16.

As best shown in FIG. 9, in the alternative embodiment, the bottom 15 of the capsule 16 is angled so that liquid flowing out of the capsule 16 is funneled out of a single break area 21 at the lowest point (the base) of capsule 16. The smaller thin-walled area 21 allows a user to break the area upon twisting. The bottom of the sleeve 12 is modified to accommodate the alternative capsule design, with the bottom plug of the capsule (portion below 21) seated in place within the bottom of the housing when the user twists, forcing the break of the weak point 21.

As shown in FIGS. 8 and 9, the alternative capsule 16 further includes a shoulder 19 to make handling of the capsule 16 easier. Additionally, unlike the preferred embodiment, there are no threads or grooves on the capsule 16 or in the interior of the sleeve 12—the capsule is seated fully within the housing. The test is initiated by a twist, forcing the capsule 16 to break as described above. Once the bottom of the capsule 16 is broken and the test is initiated, the test process proceeds as described above.

Figure 10:
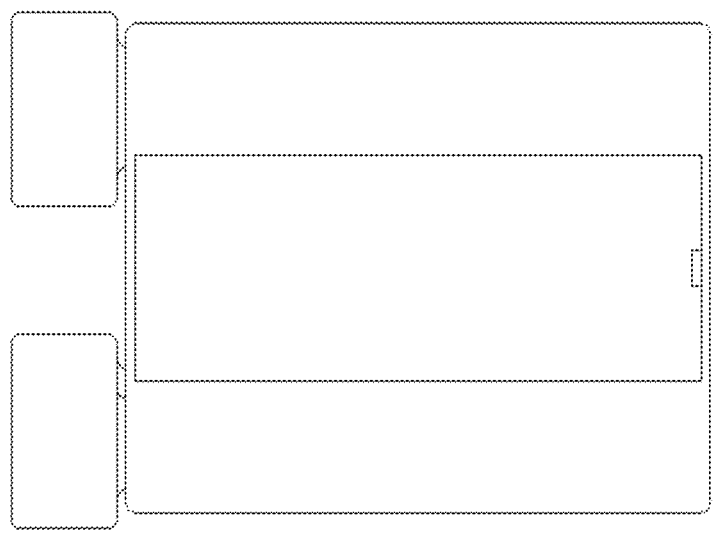
FIGS. 10 and 11 show a further alternative embodiment.
Figure 11:
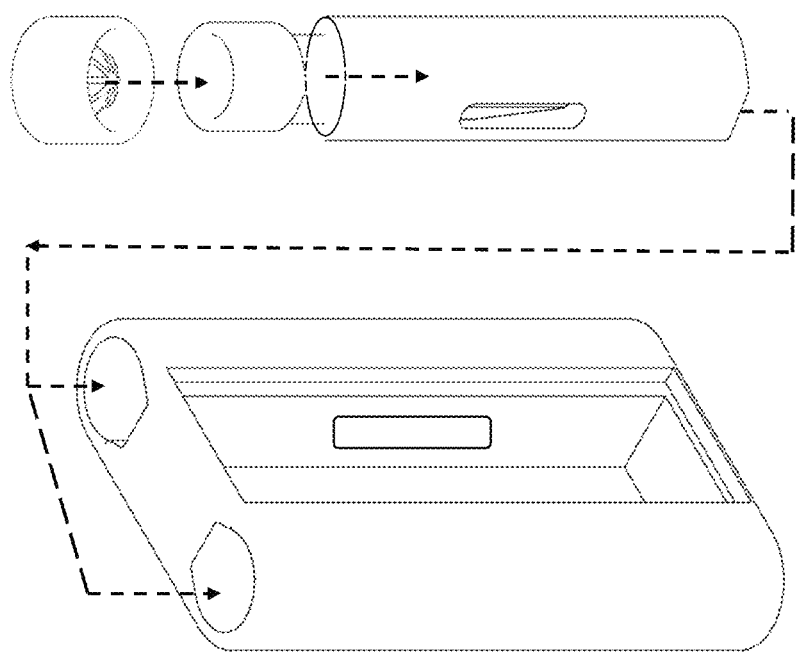

FIGS. 10 and 11 shows a simplified alternative compact design that allows a user to carry multiple test sleeves.

Figure 12:
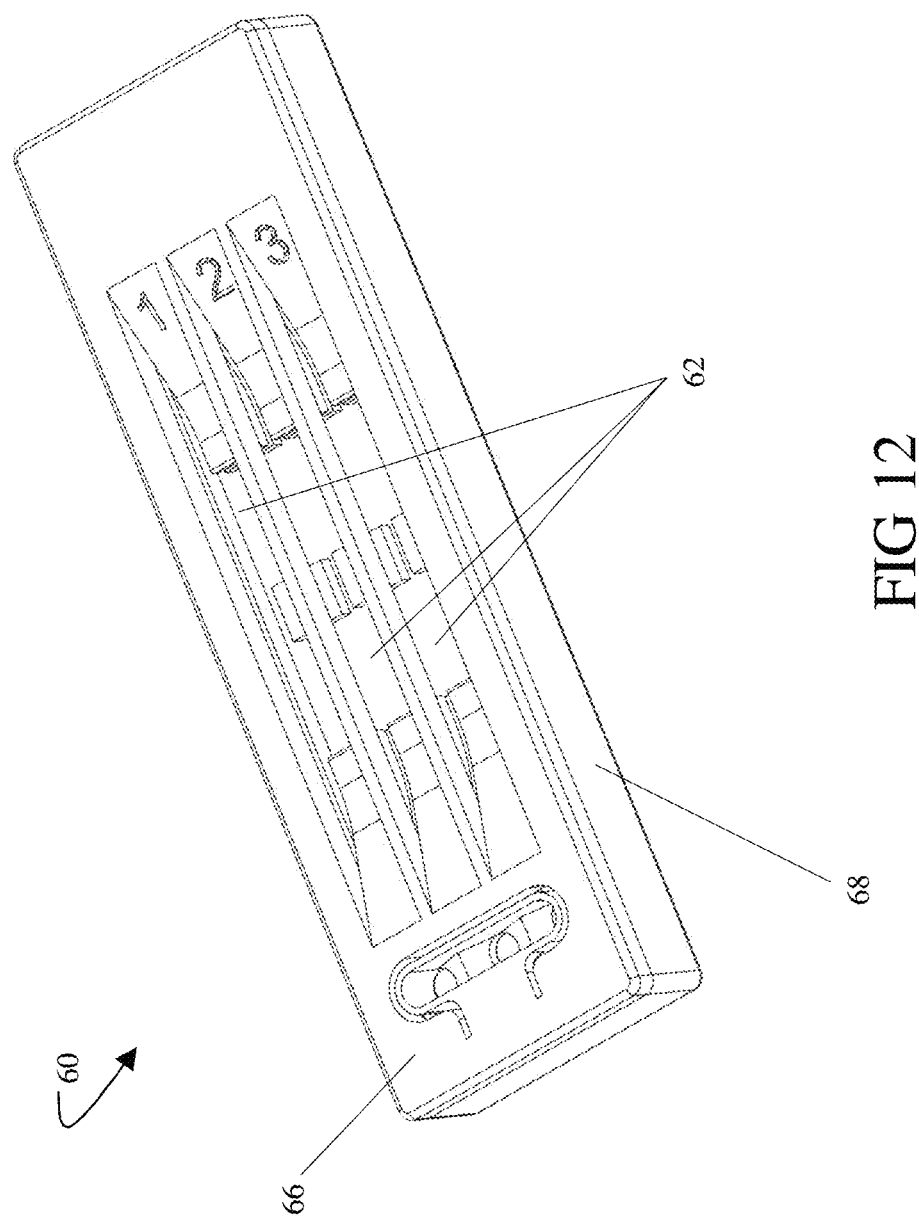
FIG. 12 shows an elevated isometric view of an additional preferred embodiment of the biosensor in the form of a multi-test strip cassette. Specifically.
Figure 13:
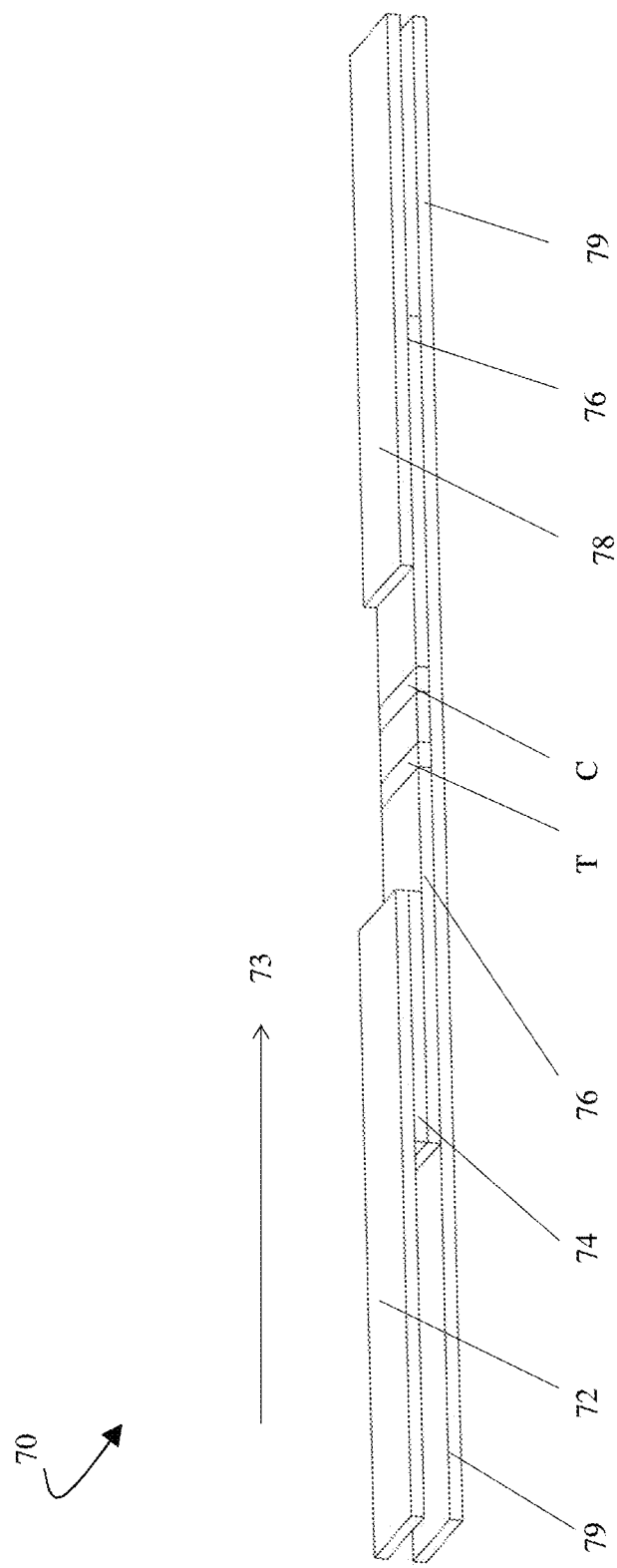
FIG. 13 shows an example of an immunochromatographic test strip of the type that may be used in the multi-test strip cassette described herein.
Figure 14:
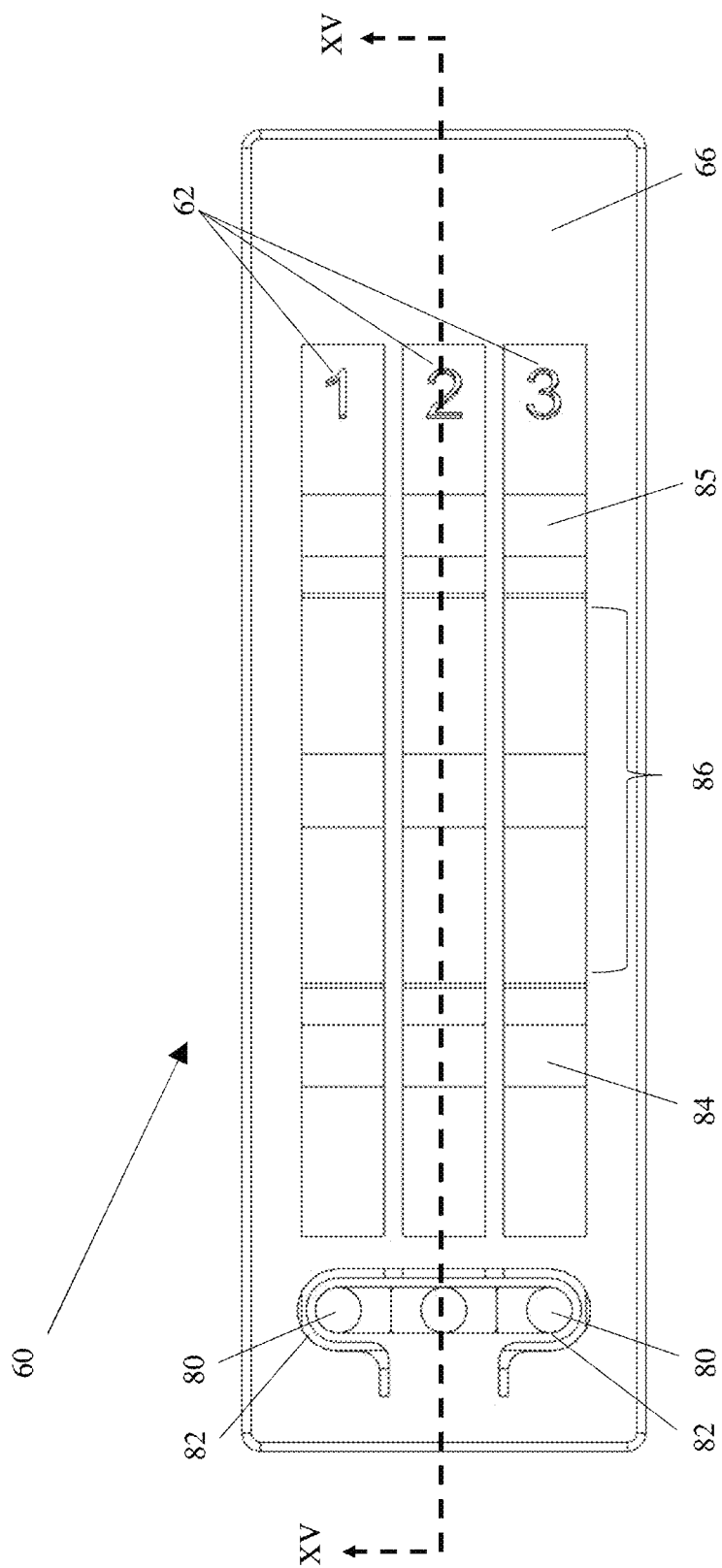
FIG. 14 shows a top view of the multi-test strip cassette shown in FIG. 12, including the section line XV-XV.

FIGS. 12-17 show an additional "3-D printable" preferred embodiment. Specifically, FIG. 12 shows a horizontally oriented biosensor that comprises a multi-strip test cassette 60. In this embodiment, the cassette 60 has multiple horizontal slots 62 designed to accommodate a plurality of immunochromatographic test strips 70 of (at least) the type shown in FIG. 13. In the preferred embodiment shown in FIG. 12, the cassette 60 has three test slots 62 and is designed to accommodate three separate test strips 70. However, in alternative embodiments there may be as few as one or two test slots 62, or as many test slots 62 as required/desired by a specific user. In the preferred embodiment, the test slots 62 are sequentially numbered—as best shown in FIGS. 12 and 14. As best shown in FIGS. 12 and 14-16, each cassette 60 comprises a top slotted cassette lid 66, and a corresponding bottom slotted cassette tray 68.

As noted supra, the multi-strip test cassette 60 is designed to accommodate industry standard immunochromatographic test strips 70. FIG. 13 shows one example of a current industry standard paper-based immunochromatographic test strip 70 which typically includes immobilized detection reagents in a dried format. The reagents are selected to react with a specific chemical and express the presence or absence of a targeted substance.

As best shown in FIG. 13, most common industry standard immunochromatographic test strips 70 comprise a "sample pad" 72 which overlaps at least a first end of a conjugate release pad 74. A second (opposite) end of the conjugate release pad 74 overlaps a first end of a nitrocellulose membrane 76. Test results are typically displayed on an intermediate portion of the nitrocellulose membrane 76 corresponding with a display window 86 in the in the cassette lid 66 (see FIG. 14) as described infra. A second (opposite) end of nitrocellulose membrane 76 overlaps an absorbent sink 78. A plastic backing strip 79 extends the length of the immunochromatographic test strip 70 and structurally stabilizes the test strip 70 and holds the test strip 70 together.

For the purposes of this disclosure, an "immunochromatographic test strip" comprises a test strip having at least one chemical reactive layer/section wherein a reagent chemical in the reactive layer reacts with an analyte to indicate (through further processing steps described infra) the presence or absence of a target substance.

For the purposes of this disclosure, "overlapping areas of the test strip" (i.e. a test strip overlap) comprises a portion of the immunochromatographic test strip 70 where at least two distinct and separate layers of a horizontally oriented test strip 70 vertically overlap. The test strip 70 is structured so that each of the layers has a different function. For example, as shown in FIG. 13, a portion of the sample pad 72 overlaps the conjugate release pad 74. Portions of the conjugate release pad 74 overlap both the sample pad 72 and the nitrocellulose membrane 76, etc.

Although FIG. 13 shows one variation of an industry standard test strip 70, one skilled in the art knows that multiple variations of the test strip 70 are common. For example, the degree of overlap between the sections/layers 72, 74, 76, 78, may vary based on the specific test analyte, the reagent, and/or the substance that is targeted by the test. Further, the test strip 70 may comprise at least two or more conjugate release sections/layers and the conjugant release reagent(s) may comprise release reagents that are not in a dried form.

In operation, as best shown in FIG. 13, a small volume of liquid analyte is applied to a designated area (usually the sample pad 72) of the immunochromatographic test strip 70. The liquid flows in the direction of the arrow 73 by capillary action to the conjugate release pad 74 where the analyte typically encounters a reagent (preferably a dried reagent) present on/in the conjugate release pad 74. The reagent reacts and mixes with the liquid analyte so that the reagent is hydrated. The hydrated reagent in combination with the analyte flows into the nitrocellulose membrane 76 and eventually into the absorbent sink 78.

As the analyte and hydrated reagent flow through the nitrocellulose membrane 76, at least one chemical "line" in the form of a "test line" T indicates the presence or absence of a target substance in the analyte. Conventionally, chemicals comprising the test line react (or do not react) with chemicals present in the hydrated reagent so that the test line T is either clearly visible, or the line is not visible. The meaning of the presence or absence of the test line T is specific to the design of the test. Although the use of a test "line" is common, other indicators such as an X, +, −, or alphabetic letters, numbers and/or symbols should be considered within the scope of the invention.

A different chemical line in the form of a "control line" C confirms that the analyte and hydrated reagent have traversed the nitrocellulose membrane 76 at least as far as the control line C so that the test process is functional and the test is assumed to be valid. As with the test line T, the composition of the control line C varies depending upon the test and visual indicators other than a control "line" C may be used to indicate that the hydrated reagent has reached a designated point on the nitrocellulose membrane 76. Finally, the absorbent sink 78 preferably absorbs any excess moisture migrating through the nitrocellulose membrane 76.

Figure 15:
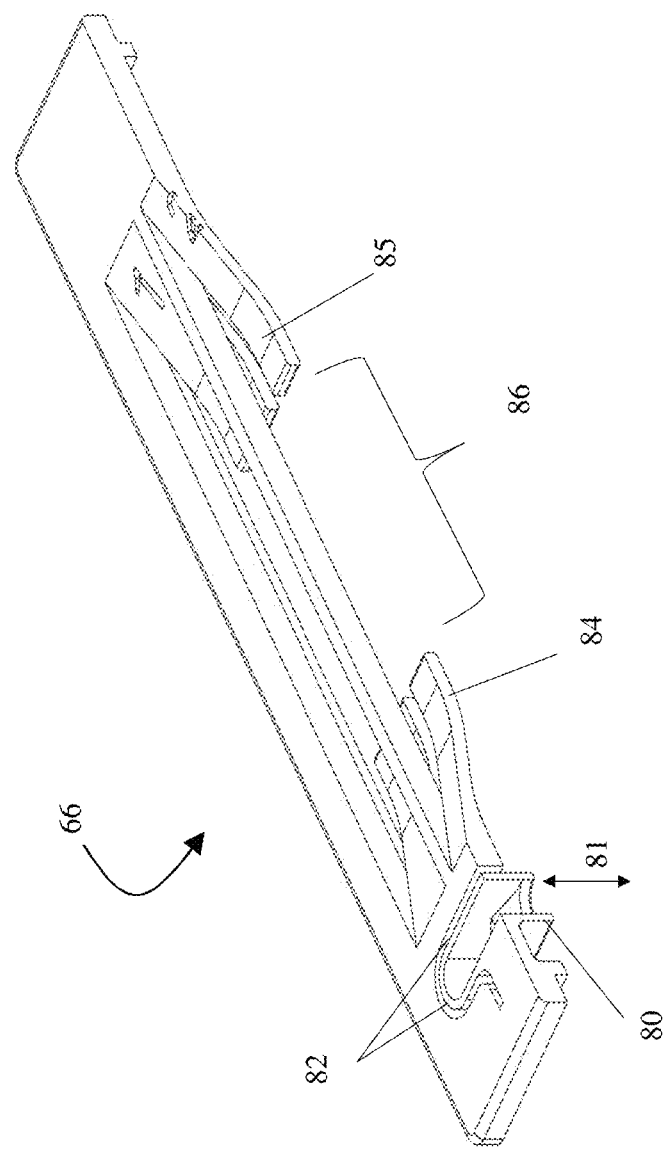
FIG. 15 is a partial sectional perspective view of the multi-test strip cassette shown in FIG. 14 along the section line XV-XV shown in FIG. 14.

As shown in FIGS. 14 and 15, in the preferred embodiment, the cassette lid 66 has a generally planar rectangular shape. As best shown in FIG. 14, the lid 66 has a flexing oval manifold 82 that extends horizontally across all the test slots 62 and comprises an analyte port 80 that corresponds with every test slot 62. The structure of the manifold 82 enables the manifold 82 to flex vertically so that the position of the base of the analyte port 80 adjusts in the direction of the arrow 81 (see FIGS. 15 and 16), and thereby allows for the use of test strips 70 having sample pads 72 of different material thicknesses. Significantly, the position of the analyte port 80 self-adjusts to the sample pad 72 vertical dimension to maintain tight contact with the sample pad 72 without material crush. The port 80 is designed to funnel a liquid analyte to the sample pad 72 and ensure that the analyte does not immediately just run off the edges of the sample pad 72.

Note that, although there are three test slots 62, for the sake of simplicity, the specific components and functions associated with only one test slot 62 will be specifically described. The other additional test slots function in the same way and should be considered duplicates of the individual test slot 62 described herein.

Figure 16:
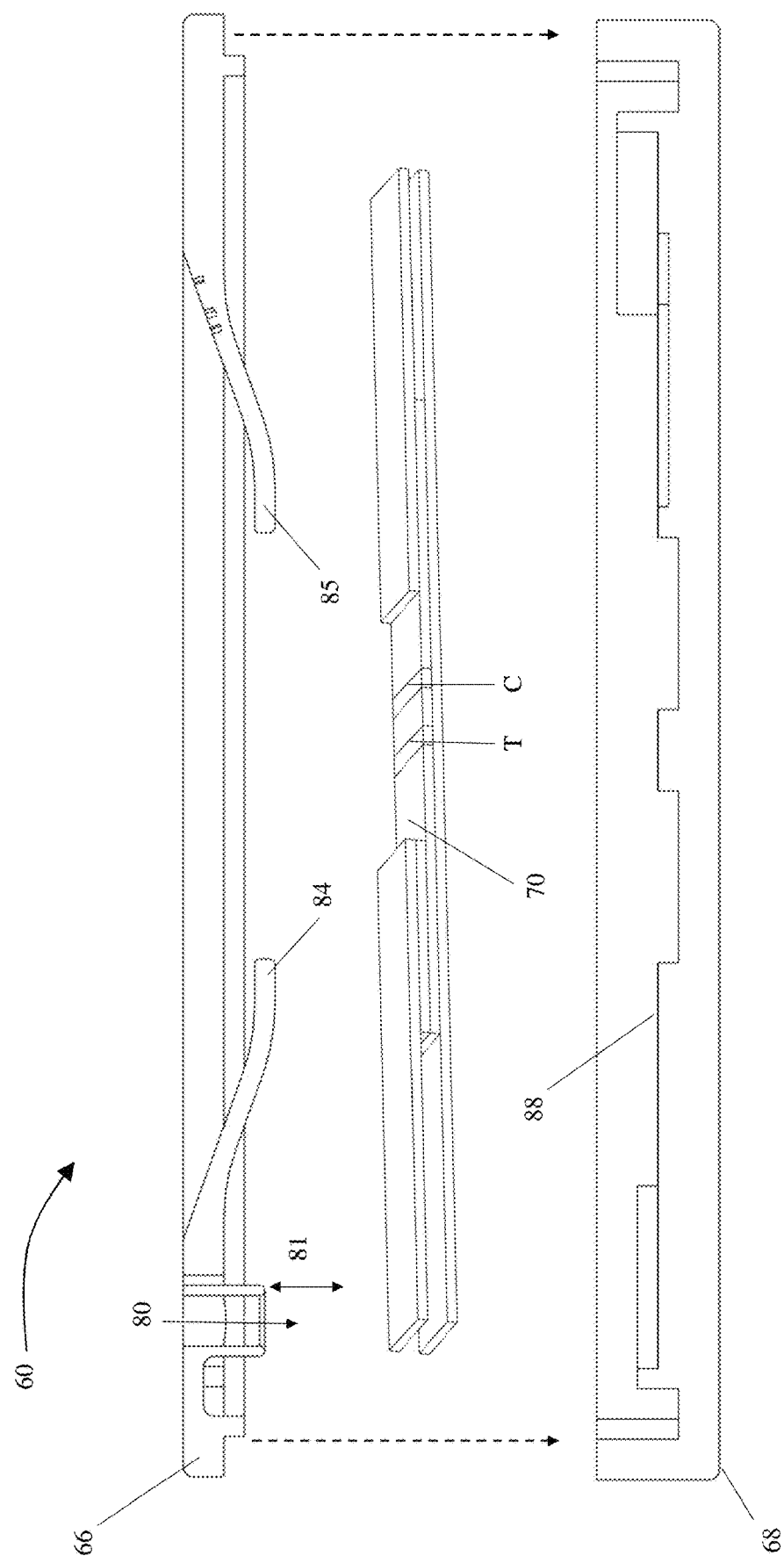
FIG. 16 is a partial sectional assembly view of the multi-test strip cassette shown in FIGS. 12-15 along the section XV-XV shown in FIG. 14.

As best shown in FIGS. 15 and 16, each test slot 62 further comprises first and second flex plates 84, 85 designed to apply a predetermined amount of pressure on the test strip 70. The structure and function of the flex plates 84, 85 is similar to previous embodiments described supra (see reference number 44 shown in at least FIGS. 3, 6, and 7). As best shown in FIG. 16, the cassette 60 is assembled, so that as the (top) cassette lid 66 snaps into the (bottom) slotted tray 68, the immunochromatographic test strip 70 is sandwiched between the flex plates 84, 85 and an elevated base 88 on the slotted tray 68. Among other things, an important function of the first and second flex plates 84, 85 is to hold the test strip 70 in place in the cassette 60 while simultaneously allowing the analyte and hydrated reagent to flow through the test strip 70 to the absorbent sink 78.

Figure 17:
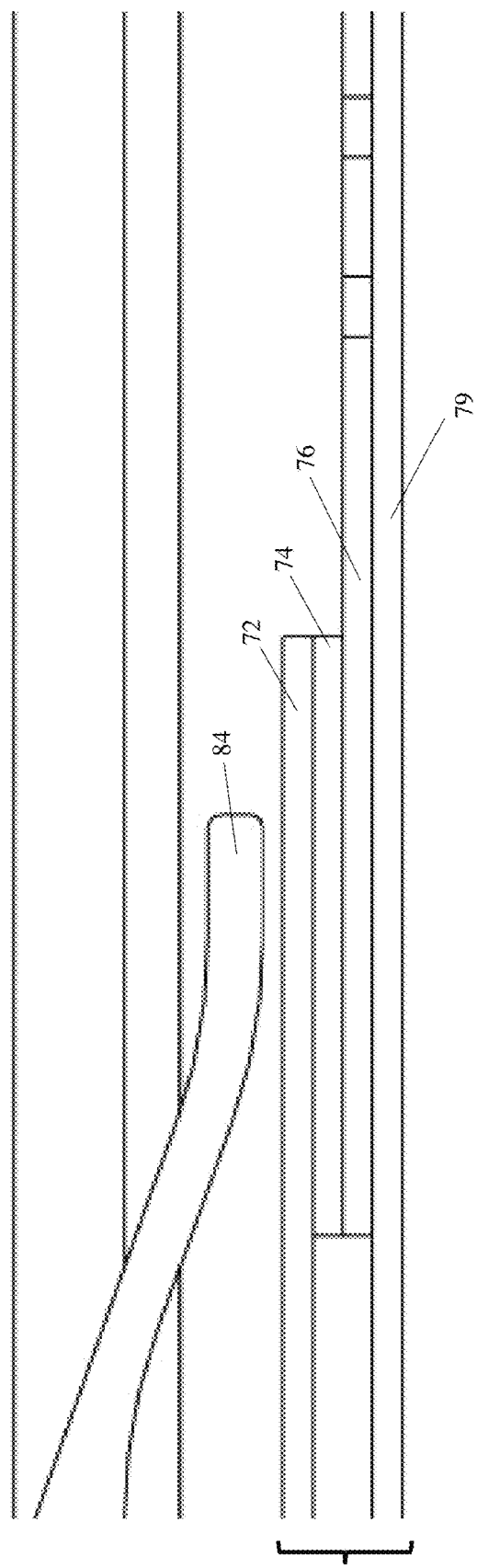
FIG. 17 is a sectional view of the flex plate as the flex plate applies pressure to the immunochromatographic test strip.

As best shown in FIG. 17, in the assembled position, the first and second flex plate 84, 85 applies a steady pressure on a selected area of the immunochromatographic test strip 70. The pressure applied to the immunochromatographic test strip 70 is self-adjusting and consistent. The force exerted on the test strip material can be controlled by changing the thickness of the plastic used in the construction of the flex plates 84, 85, where the density of plastic is proportional to force exerted. Specifically, in the preferred embodiment shown in FIGS. 13 and 17, the first flex plate 84 applies pressure in the general area of the overlap between the sample pad 72 and the conjugate release pad 74, and between the conjugate release pad 74, and the nitrocellulose membrane 76. The second flex plate 85 applies pressure to the general overlap between the absorbent sink 78, the nitrocellulose membrane, 76. As noted supra, the plastic backing 79 extends the length of the test strip. Note that, for simplicity, FIG. 17 shows spacing between flex plate 84 and the test strip 70, however, in operation, the flex plate 84 applies firm pressure on the test strip 70 in the area of the sample pad 72.

In all embodiments, at least one flex plate 84 ensures that a selected amount of firm contact is exerted between the relevant layers of the immunochromatographic test strip 70 without crushing the test strip 70 and/or blocking or hindering the capillary flow of the analyte through the test strip 70. As described supra, the flex plates 84, 85 also ensure that the immunochromatographic test strip 70 remains firmly in place. Any movement of the immunochromatographic test strip 70 during the test may skew the test results or render the test nonfunctional.

As best shown in FIG. 14-16, the lid 66 further comprises a "results display window" 86. The display window 86 essentially comprises a gap in the cassette lid 66 between the flex plates 84, 85. The test line T and control line C (as shown on the immunochromatographic test strip 70 in FIG. 13 and described supra) are visible through the results display window 86.

In alternative embodiments, an automated results detection device accesses the test results through the display window 86. For example, an imaging device (e.g. a camera) or other results detection devices (e.g. an electronic sensor analyzing/reacting to the properties of the hydrated reagent) may access the results of the test through the display window 86.

In operation, a user seeking to determine if a targeted substance is present in an analyte, selects at least one immunochromatographic test strip 70 with at least one compatible reagent present in the conjugate release pad 74, and the user ensures that the correct chemicals are impregnated into the immunochromatographic test strip 70 test T and control C lines. As best shown in FIG. 16, The selected immunochromatographic test strip 70 is placed into the test strip slot 62 and multi-test strip cassette lid 66 is snapped (or otherwise fitted) onto the slotted cassette tray 68. Specifically, the immunochromatographic test strip 70 is inserted into a test slot 62 and the strip 70 is sandwiched between the top cassette lid 66 and the bottom slotted tray 68.

A user initiates the test by directing a liquid analyte through the analyte port 80 in the oval manifold 82, and onto the immunochromatographic test strip 70 sample pad 72. The analyte flows via capillary action from the sample pad 72 into the conjugate release pad 74 where the analyte hydrates a reagent. The hydrated reagent and the analyte flow from the conjugate release pad 74 into the nitrocellulose membrane 76. As the analyte and hydrated reagent flow through immunochromatographic test strip 70, a first flex plate 84 applies a constant pressure on one or more of the overlapping sections 72, 74, 76 of the immunochromatographic test strip 70.

The analyte and the hydrated reagent continue to flow through the nitrocellulose membrane 76 in the immunochromatographic test strip 70 in the direction of the arrow 73 (see FIG. 13) until the analyte and the hydrated reagent reach the test line T. The test line T is visible through the results window 86 in the cassette lid 66. The test line T is comprised of chemicals impregnated in the nitrocellulose membrane 76 which typically react with the hydrated reagent to indicate the presence or absence of the substance targeted by the test.

As the analyte and hydrated reagent flow further through the nitrocellulose membrane 76, the analyte and the hydrated reagent reach the control line C. The control line C comprises chemicals impregnated in the nitrocellulose membrane 76 that react with the hydrated reagent to visually confirm that the analyte and hydrated reagent have traversed the nitrocellulose membrane 76 at least as far as the control line C so that the test process is functional and the test is assumed to be valid.

As the analyte and the hydrated reagent continue to flow through the nitrocellulose membrane 76, the second flex plate 85 securely holds the immunochromatographic test strip 70 in place in the test slot 62 so that the flex plate 85 overlaps the nitrocellulose membrane 76 and the liquid absorbent sink 78. The flex plates 84, 85 do not exert enough force on the immunochromatographic test strip 70 to substantially impede the flow of the analyte and the hydrated reagent but both facilitate liquid transfer between vertically oriented test strip materials. The analyte and the hydrated reagent eventually flow further through the nitrocellulose membrane 76 to the absorbent sink 76. The absorbent sink 76 absorbs any additional excess analyte and hydrated reagent liquid.

Depending upon the specific test, the test is considered functional and successfully completed at a predetermined time interval after the hydrated reagent reaches the control line C. The structure of the preferred embodiment of the multi-test strip cassette 60 enables a user to simultaneously conduct three (for example) tests as a means of confirming the results of a test and/or successfully completing the test even if one of the slots 62 indicates that a test is nonfunctional.

For the foregoing reasons, it is clear that the methods and apparatuses described herein provide multiple innovative modular biosensor systems that may be used in various applications. The current systems may be modified in multiple ways and applied in various technological applications. The disclosed methods and apparatuses may be modified and customized as required by a specific operation or application, and the individual components may be modified and defined, as required, to achieve the desired result.

Although the materials of construction are generally assumed to be various plastics, they may include a variety of compositions consistent with the function described herein. Such variations are not to be regarded as a departure from the spirit and scope of this disclosure, and all such modifications as would be obvious to one skilled in the art are intended to be included within the scope of the following claims.

The amounts, percentages and ranges disclosed herein are not meant to be absolutely limiting, and increments between the recited amounts, percentages and ranges are specifically envisioned as part of the invention. All ranges and parameters disclosed herein are understood to encompass any and all sub-ranges subsumed therein, and every number between the endpoints. For example, a stated range of "1 to 10" should be considered to include any and all sub-ranges between (and inclusive of) the minimum value of 1 and the maximum value of 10 including all integer values and decimal values; that is, all sub-ranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Similarly, if the term "about" precedes a numerically quantifiable measurement, that measurement is assumed to vary by as much as 10%. Essentially, as used herein, the term "about" refers to a quantity, level, value, or amount that varies by as much 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element which is not specifically disclosed herein.

What is claimed is:

1. A biosensor system comprising at least one test slot, each test slot comprising:
   a horizontally-extending top slotted cassette lid;
   a horizontally-extending bottom cassette tray, the cassette tray being structured so that the cassette tray connects to the cassette lid;
   a multilayer immunochromatographic test strip configured to indicate a presence or absence of a targeted substance in a selected analyte; the test strip being sandwiched between the cassette lid and the cassette tray; and
   at least one flex plate forming part of and extending downwardly from the slotted cassette lid, the at least one flex plate exerting pressure on the test strip so that the test strip is securely held in place as the analyte flows through the test strip;
   whereby, the system is structured so that, when the analyte is deposited on a designated area of the test strip, the analyte flows through the test strip and reacts with a reagent in the test strip to indicate a test result, the test result comprising an indication of a presence or absence of the targeted substance in the analyte.

2. The biosensor system of claim 1 wherein that the at least one flex plate exerts pressure on an overlap of at least two layers of the test strip.

3. The biosensor system of claim 1 wherein a horizontal portion of the at least one flex plate extends parallel with the cassette lid and exerts pressure on overlapping layers of the test strip.

4. The biosensor system of claim 1 wherein the at least one flex plate exerts self-adjusting vertical pressure on the test strip.

5. The biosensor system of claim 1 wherein the test strip is sandwiched between the at least one flex plate and an elevated base attached to the cassette tray.

6. The biosensor system of claim 1 wherein the at least one flex plate comprises a first and a second flex plate flex plates positioned in tandem in the at least one test slot.

7. The biosensor system of claim 6 wherein a first flex plate is positioned at a first end of the test strip, and a second flex plate is positioned at an opposite second end of the test strip.

8. The biosensor system of claim 6 wherein a test results window in the cassette lid is structurally positioned between the first flex plate and the second flex plate.

9. The biosensor system of claim 8 wherein the cassette lid is configured so that the test strip is visible through the test results window.

10. The biosensor system of claim 8 wherein the cassette lid is configured to contain a flexible manifold so that the manifold flexes vertically based on a thickness of the test strip.

11. The biosensor system of claim 8 wherein an automated test result detection device accesses the test result through the test results window.

12. The biosensor system of claim 1 wherein the designated area on the test strip where the analyte is deposited-comprises a sample pad.

13. The biosensor system of claim 1 wherein the test strip comprises at least one conjugant release layer, the at least one conjugant release layer comprising the reagent.

14. The biosensor system of claim 13 wherein the test strip comprises a sample pad layer, the sample pad layer overlapping the at least one conjugant release layer, the at least one conjugant release layer overlapping the sample pad and a nitrocellulose membrane layer, the nitrocellulose membrane layer overlapping the at least one conjugant release layer and an absorbent sink layer.

15. The biosensor system of claim 14 wherein a chemical test line on the nitrocellulose membrane layer indicates the test result.

16. The biosensor system of claim 15 wherein a chemical control line on the nitrocellulose membrane indicates whether the analyte in combination with the reagent have flowed through the test strip at least as far as the control line.

17. The biosensor system of claim 1 wherein the system is configured to comprise multiple test slots, each test slot comprising a single test strip so that multiple test slots are arranged in parallel, the system being structured so that multiple tests are conducted simultaneously.

18. A method of determining a presence or absence of a targeted substance in an analyte, the method comprising the steps of:
   (a) providing the system of claim 1;
   (b) depositing an analyte on the designated area of the test strip;
   (c) reading the test result indicated on the test strip.

19. The method of claim 18 wherein, in step (a), the system comprises at least two flex plates, a test results window in the cassette lid being positioned between the at least two flex plates, the test result being indicated on the test strip, and the test strip being visible through the test results window.

20. The method of claim 19 wherein, in step (c) an automated test result detection device accesses the test result through the test results window.

* * * * *